US00PP36119P2

(12) United States Plant Patent
van Dijk

(10) Patent No.: US PP36,119 P2
(45) Date of Patent: Sep. 17, 2024

(54) ***HYDRANGEA* PLANT NAMED 'HIHALO59'**

(50) Latin Name: *Hydrangea macrophylla*
Varietal Denomination: HIHALO59

(71) Applicant: Roy Robin van Dijk, De Lier (NL)

(72) Inventor: Roy Robin van Dijk, De Lier (NL)

(73) Assignee: HI BREEDING B.V., De Lier (NL)

( * ) Notice: Subject to any disclaimer, the term of this patent is extended or adjusted under 35 U.S.C. 154(b) by 0 days.

(21) Appl. No.: 18/534,606

(22) Filed: Dec. 9, 2023

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/02; A01H 5/00; A01H 6/48
See application file for complete search history.

(56) References Cited

U.S. PATENT DOCUMENTS

PP16,441 P2 * 4/2006 Arts ..... A01H 6/48
Plt./250
PP34,800 P2 * 12/2022 van Dijk ..... Plt./250

OTHER PUBLICATIONS

*Hydrangea* Breeders Association 2020 Catalogus, retrieved on Apr. 17, 2024 at https://www.hydrangeabreeders.nl/wp-content/uploads/2021/01/2020-Catalogus-HBA-potplanten-paniculata.pdf, 16 pp. (Year: 2020).*

* cited by examiner

*Primary Examiner* — June Hwu
(74) *Attorney, Agent, or Firm* — C. Anne Whealy

(57) ABSTRACT

A new and distinct cultivar of Hydrangea plant named 'HIHALO59', characterized by its upright and broadly spreading plant habit; moderately vigorous and moderate growth rate; freely branching habit; strong and sturdy stems; dark green-colored leaves; freely flowering habit; large and dense mophead inflorescences with purplish pink-colored sterile flowers; and good post-production longevity.

2 Drawing Sheets

Figure 1:
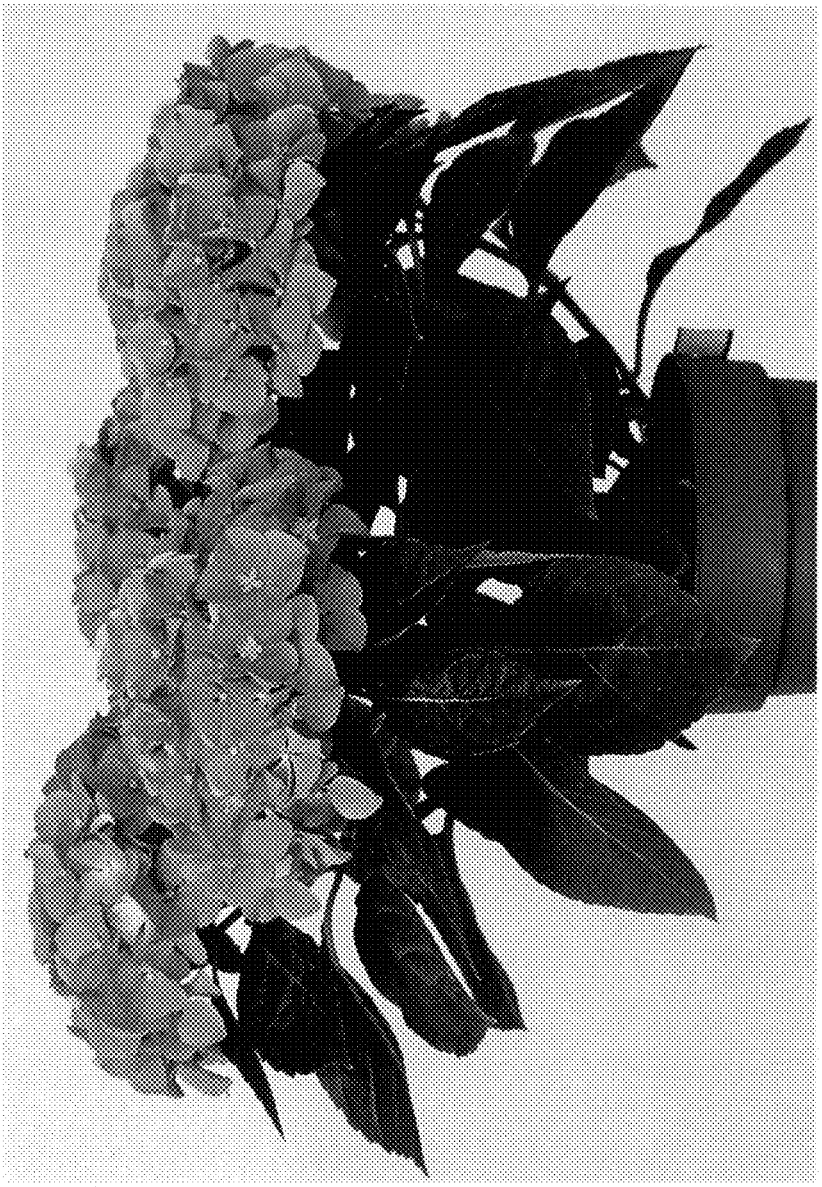

Botanical designation: *Hydrangea macrophylla.*
Cultivar denomination: 'HIHALO59'.

STATEMENT REGARDING PRIOR DISCLOSURES BY INVENTOR/APPLICANT & ASSIGNEE

An United Kingdom Plant Breeder's Rights application for the instant plant was filed by the Assignee of the instant application, Hi Breeding B.V. of De Lier, The Netherlands on Nov. 11, 2022, application No. 23/799. Foreign priority is not claimed to this United Kingdom Plant Breeder's Rights application.

An European Community Plant Breeder's Rights application for the instant plant was filed by the Assignee of the instant application, Hi Breeding B.V. of De Lier, The Netherlands on Jul. 4, 2023, application No. 2023/1464. Foreign priority is not claimed to this European Plant Breeder's Rights application.

The Inventor/Applicant and Assignee assert that no sales, offers for sale or public distribution of the instant plant occurred more than one year prior to the effective filing date of this application.

Any information about the claimed plant would have been obtained from a direct or indirect disclosure from the Inventor/Applicant and/or Assignee. Inventor/Applicant and Assignee claim a prior art exception under 35 U.S.C. 102 (b)(1) for disclosures and/or sales prior to the filing date but less than one year prior to the effective filing date.

BACKGROUND OF THE INVENTION

The present invention relates to a new and distinct cultivar of Hydrangea plant, botanically known as *Hydrangea macrophylla*, commercially referred to as a mophead-type Hydrangea and hereinafter referred to by the name 'HIHALO59'.

The new Hydrangea plant is a product of a planned breeding program conducted by the Inventor in De Lier, The Netherlands. The objective of the breeding program is to create new sturdy and strong Hydrangea plants with attractive inflorescences and good postproduction longevity.

The new Hydrangea plant originated from an open-pollination in Apr. 2016 of a proprietary selection of *Hydrangea macrophylla* identified as code No. 1459, not patented, as the female, or seed, parent with an unknown proprietary selection of *Hydrangea macrophylla* as the male, or pollen, parent. The new Hydrangea plant was discovered and selected as a single flowering plant from within the progeny of the stated open-pollination in a controlled greenhouse environment in De Lier, The Netherlands in Apr. 2018.

Asexual reproduction of the new Hydrangea plant by terminal vegetative cuttings since Jul. 2018 in a controlled greenhouse environment in De Lier, The Netherlands has shown that the unique features of this new Hydrangea plant are stable and reproduced true to type in successive generations of asexual reproduction.

SUMMARY OF THE INVENTION

Plants of the new Hydrangea have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HIHALO59'. These characteristics in combination distinguish 'HIHALO59' as a new and distinct Hydrangea plant:

1. Upright and broadly spreading plant habit.
2. Moderately vigorous and moderate growth rate.
3. Freely branching habit.
4. Strong and sturdy stems.
5. Dark green-colored leaves.
6. Freely flowering habit.
7. Large and dense mophead inflorescences with purplish pink-colored sterile flowers.
8. Good post-production longevity.

Plants of the new Hydrangea can be compared to plants of the female parent selection. Plants of the new Hydrangea differ primarily from plants of the female parent selection in the following characteristics:

1. Plants of the new Hydrangea have sturdier stems than plants of the female parent selection.
2. Plants of the new Hydrangea respond well to being "blued" with aluminum sulfate whereas plants of the female parent selection do not respond well to being "blued".

Plants of the new Hydrangea can be compared to plants of *Hydrangea macrophylla* 'HBA 202911', trade name for '200749077' (U.S. Plant Pat. No. 16,441). In side-by-side comparisons, plants of the new Hydrangea differ primarily from plants of 'HBA 202911' in stem strength as stems of plants of the new Hydrangea are sturdier than stems of plants of 'HBA 202911'. In addition, plants of the new Hydrangea are more upright than plants of 'HBA 202911'.

Plants of the new Hydrangea can also be compared to plants of *Hydrangea macrophylla* 'HIOCE', disclosed in U.S. Plant Pat. No. 34,800. In side-by-side comparisons, plants of the new Hydrangea differ primarily from plants of 'HIOCE' in plant habit as plants of the new Hydrangea are more upright than plants of 'HIOCE'. In addition, sterile flowers of plants of the new Hydrangea are purplish pink in color whereas sterile flowers of plants of 'HIOCE' are purplish red in color.

BRIEF DESCRIPTION OF THE PHOTOGRAPHS

Figure 2:
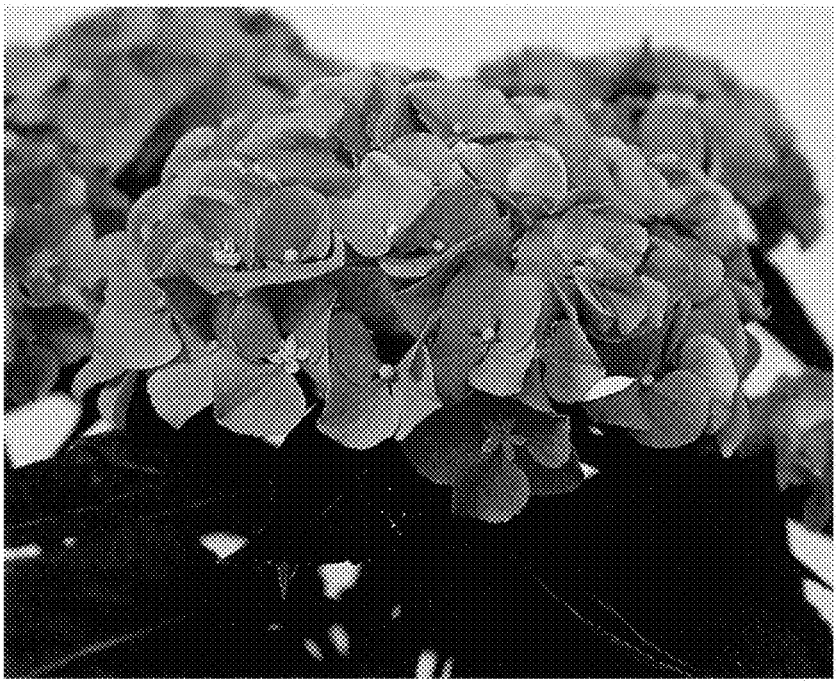

The accompanying colored photographs illustrate the unique appearance of the new Hydrangea plant showing the colors as true as it is reasonably possible to obtain in colored reproductions of this type. Colors in the photographs may differ from the color values cited in the detailed botanical description which accurately describe the colors of the new Hydrangea plant. The photograph on the first sheet (FIG. 1) is a side perspective view of a typical flowering plant of 'HIHALO59' grown in a container. The photograph on the second sheet (FIG. 2) is a close-up view of a typical flowering plant of 'HIHALO59'.

DETAILED BOTANICAL DESCRIPTION

Plants used in the aforementioned photographs and in the following description were grown during the late summer in 13-cm containers in a glass-covered greenhouse in De Lier, The Netherlands and under cultural practices typical of commercial Hydrangea production. During the production of the plants, day temperatures ranged from 20C to 35C, night temperatures ranged from 10C to 22C and light levels averaged 4,000 lux. Plants of the new Hydrangea were pinched one time and were 18 months old when the photographs and description were taken. In the following description, color references are made to The Royal Horticultural Society Colour Chart, 2015 Edition, except where general terms of ordinary dictionary significance are used. Plants of the new Hydrangea can be treated with aluminum sulfate to "blue" the flower color.

Botanical description:

*Hydrangea macrophylla*.—'HIHALO59'.

Parentage:

*Female, or seed, patent*.—Proprietary selection of *Hydrangea macrophylla* identified as code No. 1459, not patented.

*Male, or pollen, patent*.—Unknown proprietary selection of *Hydrangea macrophylla*.

Propagation:

*Type cutting*.—By vegetative terminal cuttings.

*Time to initiate roots, summer*.—About twelve days at temperatures about 22C.

*Time to initiate roots, winter*.—About 14 days at temperatures about 20C.

*Time to produce a rooted young plant, summer*.—About 28 days at temperatures about 22C.

*Time to produce a rooted young plant, winter*.—About 30 days at temperatures about 19C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright, broadly outwardly spreading and mounding plant habit; flattened globular in overall shape; strong and sturdy stems; moderately vigorous growth habit and moderate growth rate; about six months from propagation are required to produce small finished flowering plants.

*Plant height*.—About 27.2 cm.

*Plant diameter or area of spread*.—About 41.6 cm.

Lateral branch description:

*Branching habit*.—Freely branching habit with about six lateral branches per plant; pinching enhances lateral branch development.

*Length*.—About 11 cm.

*Diameter*.—About 6 mm.

*Internode length*.—About 2.5 cm.

*Strength*.—Strong, sturdy.

*Aspect*.—About 20 to 90 degrees from vertical.

*Texture*.—Smooth, glabrous; becoming woody with development.

*Color, developing*.—Close to 144A to 144B.

*Color, fully developed*.—Close to 144A; when woody, close to 199A to 199C, N199C and N199D.

*Lenticels*.—Density: Sparse to moderate. Length: About 1 mm. Diameter: About 0.5 mm. Color: Close to a blend of N186C and 200A.

Leaf description:

*Arrangement*.—Opposite, simple.

*Length*.—About 10.8 cm.

*Width*.—About 7.9 cm.

*Shape*.—Broadly ovate.

*Apex*.—Apiculate.

*Base*.—Short attenuate to attenuate.

*Margin*.—Dentate-crenate.

*Texture, upper surface*.—Slightly rugose, glabrous.

*Texture, lower surface*.—Moderately rugose, glabrous.

*Venation pattern*.—Pinnate.

*Color*.—Developing leaves, upper surface: Close to 137A. Developing leaves, lower surface: Close to a blend of 138A and 147B. Fully developed leaves, upper surface: Close to NN137A; venation, close to 146B. Fully developed leaves, lower surface: Close to 147B; venation, close to 146D.

*Petioles*.—Length: About 2.4 cm. Diameter: About 3 mm to 4 mm. Texture and luster, upper and lower surfaces: Smooth, glabrous; slightly glossy. Color, upper surface: Close to 144A. Color, lower surface: Close to 146B to 146C.

Flower description:

*Flower type and habit*.—Showy rotate sterile flowers and small, inconspicuous rotate fertile flowers arranged on mophead-type terminal panicles; panicles flattened globular in shape; sterile flowers face upright to outwardly, fertile flowers face mostly upright.

*Fragrance*.—None detected.

*Natural flowering season*.—In the garden, plants flower continuously from the late spring to late summer in The Netherlands; flower dormancy can be broken with a cold storage treatment.

*Flower longevity*.—Good postproduction longevity; sterile flowers maintain good substance for about six weeks on the plant, sterile flowers persistent; fertile flowers last for a few days on the plant, fertile flowers not persistent.

*Quantity of flowers*.—Freely flowering habit; about 120 sterile flowers per panicle and about 70 fertile flowers per panicle.

*Panicle height*.—About 10.2 cm.

*Panicle diameter*.—About 15.2 cm.

*Panicle peduncles*.—Length: About 4.6 cm. Diameter: About 3.75 mm. Strength: Strong. Aspect: Primary peduncles, mostly erect; lateral peduncles, about 35 degrees from primary peduncle axis. Texture: Moderately pubescent. Color: Close to 182D; towards the base, close to 147D.

*Sterile flower buds*.—Length: About 9 mm. Diameter: About 1.9 cm. Shape: Broadly cup-shaped. Color: Close to 63C to 63D and towards the base, close to 150D; when "blued", close to N88C to N88D and towards the base, close to 150D.

*Fertile flower buds*.—Length: About 5 mm. Diameter: About 5 mm. Shape: Globular. Color: Close to 75C; when "blued", close to 97D.

*Sterile flower diameter*.—About 3.5 cm to 4 cm.

*Sterile flower depth* (*height*).—About 9 mm to 20 mm.

*Fertile flower diameter*.—About 1.4 cm.

*Fertile flower depth* (*height*).—About 9 mm.

*Petals, sterile flowers*.—Quantity and arrangement: Four or five, in a single whorl. Length: About 5 mm. Width: About 3 mm. Shape: Ovate, moderately concave. Apex: Acute. Base: Cuneate. Margin: Entire. Texture and luster, upper and lower surfaces: Smooth, glabrous; matte. Color: When opening, upper surface: Close to 70C; when "blued", close to 98C. When opening, lower surface: Close to 68B to 68C; when "blued", close to 98B. Fully opened, upper surface: Close to 70D; when "blued", close to 98C to 98D; color does not change with subsequent development. Fully opened, lower surface: Close to 70D; when "blued", close to 98B to 98C; color does not change with subsequent development.

*Petals, fertile flowers*.—Quantity and arrangement: About five in a single whorl. Length: About 6 mm. Width: About 3 mm. Shape: Ovate, concave. Apex: Acute. Base: Cuneate. Margin: Entire. Texture and luster, upper and lower surfaces: Smooth, glabrous; matte. Color: When opening, upper surface: Close to 70C; when "blued", close to 98C. When opening, lower surface: Close to 68B to 68C; when "blued", close to 98B. Fully opened, upper surface: Close to 70D; when "blued", close to 98C to 98D; color does not change with subsequent development. Fully opened, lower surface: Close to 70D; when "blued", close to 98B to 98C; color does not change with subsequent development.

*Sepals, sterile flowers*.—Quantity and arrangement: Typically four or five, or rarely six, in a single whorl; moderately to strongly imbricate. Length: About 2 cm. Width: About 2.1 cm. Shape: Reniform to close to broadly deltoid; slightly concave. Apex: Broadly and bluntly acute to retuse. Base: Cuneate. Margin: Entire to shallowly crenate; slightly coarsely undulate. Texture and luster, upper and lower surfaces: Smooth, glabrous; matte. Color: When opening, upper surface: Close to 68B; when "blued", close to N82B. When opening, lower surface: Close to 73C; when "blued", close to N82B and towards the margins and apex, close to 94C to 94D. Fully opened, upper surface: Close to 68B and towards the base, close to 68A; when "blued", close to 94B tinged with close to N87B; color does not change with subsequent development. Fully opened, lower surface: Close to 73B; when "blued", close to 91A; color does not change with subsequent development.

*Sepals, fertile flowers*.—Quantity and arrangement: Five in a single whorl. Length: About 2.75 mm. Width: About 2 mm. Shape: Broadly ovate to broadly elliptic. Apex: Acute. Base: Cuneate. Margin: Entire. Texture and luster, upper and lower surfaces: Smooth, glabrous; matte. Color: When opening, upper surface: Close to 145D and towards the margins, close to 63D; when "blued", close to 145C to 145D and towards the margins, close to 102B. When opening, lower surface: Close to 149C and towards the margins, close to 63B to 63C; when "blued", close to 145B and towards the margins, close to 102B. Fully opened, upper surface: Close to 65D and apices, close to 145D; when "blued", close to 92B to 92C; color does not change with subsequent development. Fully opened, lower surface: Close to 145D and margins, close to 73C; when "blued", close to 100D; color does not change with subsequent development.

*Pedicels, sterile flowers*.—Length: About 2 cm. Diameter: About 1.2 mm. Strength: Moderately strong. Aspect: About 35 degrees from main peduncle axis Texture and luster: Moderately pubescent; matte. Color: Close to 63C; when "blued", close to 94D.

*Pedicels, fertile flowers*.—Length: About 7 mm. Diameter: About 1 mm. Strength: Moderately strong.

Aspect: About 5 degrees from vertical. Texture and luster: Sparsely pubescent; matte. Color: Close to N75A to N75B; when "blued", close to 98B.

*Reproductive organs, sterile flowers*.—Stamens: Quantity per flower: About eight to ten. Filament length: About 4 mm. Filament color: Close to 69D; when "blued", close to N155A. Anther length: About 1 mm. Anther shape: Broadly oblong. Anther color: Close to 69B; when "blued", close to 102D. Pollen amount: Moderate. Pollen color: Close to 156A. Pistils: Pistil quantity per flower: About two or three. Pistil length: About 1.25 mm. Stigma shape: Club-shaped. Stigma color: Close to 69C to 69D; when "blued", close to 108D. Style length: About 1 mm. Style color: Close to 65A to 65C; when "blued", close to 100C to 100D. Ovary color: Close to 150D; when "blued", close to 150D.

*Reproductive organs, fertile flowers*.—Stamens: Quantity per flower: About 10 to 13. Filament length: About 5 mm. Filament color: Close to 69D; when "blued", close to N155A. Anther length: About 5 mm. Anther shape: Broadly oblong. Anther color: Close to 69B; when "blued", close to 102D. Pollen amount: Moderate. Pollen color: Close to 156A. Pistils: Pistil quantity per flower: About three, occasionally two to four. Pistil length: About 1.5 mm. Stigma shape: Club-shaped. Stigma color: Close to 69C to 69D; when "blued", close to 108D. Style length: About 1.25 mm. Style color: Close to 65A to 65C; when "blued", close to 100C to 100D. Ovary color: Close to 150D; when "blued", close to 150D.

*Seeds*.—To date, seed development has not been observed on plants of the new Hydrangea.

Pathogen & pest resistance: Plants of the new Hydrangea have been observed to be tolerant to Botrytis (*Botrytis cinerea*). To date, plants of the new Hydrangea have not been observed to be resistant to pests and other pathogens common to Hydrangea plants.

Temperature tolerance: Plants of the new Hydrangea have been shown to be suitable for USDA Hardiness Zones 5 through 9.

It is claimed:

1. A new and distinct Hydrangea plant named 'HIHALO59' as illustrated and described.

* * * * *